(12) United States Patent
Kim et al.

(10) Patent No.: US 11,817,203 B2
(45) Date of Patent: Nov. 14, 2023

(54) ULTRASOUND CLINICAL FEATURE DETECTION AND ASSOCIATED DEVICES, SYSTEMS, AND METHODS

(71) Applicant: KONINKLIJKE PHILIPS N.V., Eindhoven (NL)

(72) Inventors: Seungsoo Kim, Andover, MA (US); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 741 days.

(21) Appl. No.: 16/498,667

(22) PCT Filed: Mar. 28, 2018

(86) PCT No.: PCT/EP2018/058030
§ 371 (c)(1),
(2) Date: Sep. 27, 2019

(87) PCT Pub. No.: WO2018/178212
PCT Pub. Date: Oct. 4, 2018

(65) Prior Publication Data
US 2020/0043602 A1 Feb. 6, 2020

Related U.S. Application Data

(60) Provisional application No. 62/477,536, filed on Mar. 28, 2017.

(51) Int. Cl.
*G16H 30/40* (2018.01)
*G16H 50/20* (2018.01)
(Continued)

(52) U.S. Cl.
CPC ............. *G16H 30/40* (2018.01); *A61B 8/483* (2013.01); *G06N 3/02* (2013.01); *G06N 20/00* (2019.01);
(Continued)

(58) Field of Classification Search
CPC ........ G16H 30/40; G16H 50/20; G16H 50/70; G06N 20/03; G06N 3/02; A61B 8/483;
(Continued)

(56) References Cited

U.S. PATENT DOCUMENTS 7,738,683 B2 * 6/2010 Cahill .................. G06T 7/0012
382/128
9,589,374 B1 3/2017 Gao et al.
(Continued)

FOREIGN PATENT DOCUMENTS

WO 2016046140 A1 3/2016
WO 2016193979 A1 12/2016

OTHER PUBLICATIONS

Chen et al. "Automatic Fetal Ultrasound Standard Plane Detection Using Knowledge Transferred Recurrent Neural Networks", Medical Image Computing and Computer-Assisted Intervention—MICCAI 2015. (Year: 2015).*
(Continued)

*Primary Examiner* — Amandeep Saini
*Assistant Examiner* — Julius Chai

(57) ABSTRACT

Ultrasound image devices, systems, and methods are provided. A clinical condition detection system, comprising a communication device in communication with an ultrasound imaging device and configured to receive a sequence of ultrasound image frames representative of a subject body across a time period; and a processor in communication with the communication device and configured to classify the sequence of ultrasound image frames into a first set of
(Continued)

clinical characteristics by applying a first predictive network to the sequence of ultrasound image frames to produce a set of classification vectors representing the first set of clinical characteristics; and identify a clinical condition of the subject body by applying a second predictive network to the set of classification vectors.

12 Claims, 7 Drawing Sheets

(51) Int. Cl.
  G06N 20/00      (2019.01)
  A61B 8/08       (2006.01)
  G06N 3/02       (2006.01)
  G16H 50/70      (2018.01)
  G06T 7/00       (2017.01)

(52) U.S. Cl.
  CPC ........... *G16H 50/20* (2018.01); *G06T 7/0012* (2013.01); *G06T 2207/30061* (2013.01); *G06V 2201/03* (2022.01); *G16H 50/70* (2018.01)

(58) Field of Classification Search
  CPC .............. G06V 2201/03; G06T 7/0012; G06T 2207/30061
  See application file for complete search history.

(56) References Cited

U.S. PATENT DOCUMENTS

| 9,636,081    | B2 * | 5/2017  | Reuter ................. A61B 5/7264 |
| 2015/0379709 | A1 * | 12/2015 | Liang ........................ G06T 7/40 382/131 |
| 2016/0171683 | A1 * | 6/2016  | Lee ........................ G16H 50/70 382/128 |
| 2016/0239959 | A1 * | 8/2016  | Blackbourne .......... G06V 10/40 |
| 2016/0350620 | A1   | 12/2016 | Rao et al. |
| 2017/0360412 | A1 * | 12/2017 | Rothberg ............... A61B 8/065 |
| 2018/0028079 | A1 * | 2/2018  | Gurevich ............. A61B 5/7232 |
| 2018/0075597 | A1 * | 3/2018  | Zhou ...................... G06N 20/00 |
| 2018/0263568 | A1 * | 9/2018  | Yi ..................... A61B 1/000094 |
| 2019/0180153 | A1 * | 6/2019  | Buckler ............... G06V 20/698 |
| 2019/0333216 | A1 * | 10/2019 | Isgum ................... G16H 50/50 |
| 2019/0388064 | A1 * | 12/2019 | Kezurer ................ G16H 50/20 |

OTHER PUBLICATIONS

PCT International Search Report, International application No. PCT/EP2018/058030, dated Jul. 27, 2018.
Letter and Amendment in Response to the International Search Report and the Written Opinion of the International Searching Authority Under Article 34, David Rodack, dated Nov. 27, 2018.
B0cchi L et al., "Semiautomated Breast Cancer Classification from Ultrasound Video", Bi0medical Imaging (ISBI), 2012 9th IEEE Internati0nal Symp0sium 0n, IEEE, May 2, 2012 (May 2, 2012), pp. 1112-1115, XP032199212.
Y. Ga0 et al., "Describing Ultrasound Video Content Using Deep Convolutional Neural Networks", 2016, IEEE 13th Internati0nal Symp0sium 0n Bi0medical Imaging (ISBI), Apr. 1, 2016 (Apr. 1, 2016), pp. 787-790, XP55491075.
Kumar D Ashok et al., "Investigations on Severity Level for Diabetic Maculopathy Based on the Location of Lesions", 2017 W0rld C0ngress 0n C0mputing and C0mmunication Techn0l0gies (WCCCT), IEEE, Feb. 2, 2017 (Feb. 2, 2017), pp. 127-131, XP033229233.
Kh0baib Zaam0ut et al., "Improving Neural Networks Classification through Chaining", Sep. 11, 2012 (Sep. 11, 2012), Artificial Neural Netw0rks and Machine Learning ICANN 2012, Springer Berlin Heidelberg, Berlin, Heidelberg, pp. 288-295, XP047017748.

\* cited by examiner

ULTRASOUND CLINICAL FEATURE DETECTION AND ASSOCIATED DEVICES, SYSTEMS, AND METHODS

CROSS-REFERENCE TO RELATED APPLICATION

This patent application claims the priority benefit under 35 U.S.C. § 371 of International Patent Application no. PCT/EP2018/058030, filed Mar. 28, 2018, which claims the benefit of U.S. Application Ser. No. 62/477,536, filed on Mar. 28, 2017. These applications are hereby incorporated by reference herein in their entirety.

TECHNICAL FIELD

The present disclosure relates generally to ultrasound imaging and, in particular, to providing automated systems and methods for detecting clinical features for assessments of various clinical conditions and/or diseases.

BACKGROUND

Lung ultrasound examinations can provide indications for clinical conditions including pulmonary diseases, such as pneumonia, pneumothorax, and acute respiratory distress syndrome (ARDS), and congestive heart failures. For example, a clinician or a physician may perform an ultrasound examination on a patient by acquiring ultrasound images of the patient and determine whether the patient may have a certain clinical condition based on features identified from the ultrasound images. Examples of lung ultrasound image features may include B-line artifacts, consolidation, air bronchogram, and/or pleural effusion. The presence of any such feature may indicate a particular lung condition or disease, whereas the absence of these features may indicate a normal healthy lung. An experienced ultrasound user may easily identify such lung ultrasound image features from an acquired ultrasound image. However, a non-experienced user or a less experienced user may have difficulties in interpreting acquired images. The lack of standardization and/or quantification in such clinical assessment procedures can lead to different results even among experienced users. As such, additional examinations, such as X-ray, are often required subsequent to an ultrasound examination.

SUMMARY

While existing ultrasound imaging has proved useful for clinical assessments and diagnosis, there remains a clinical need for improved systems and techniques for providing automated clinical diagnostic tools. Embodiments of the present disclosure provide a deep learning framework for automatic ultrasound image video classification. The classification can be used to assist a clinical assessment. The classification includes a frame-by-frame classification for a spatial feature analysis, followed by a time-series vector analysis. For example, the video may include a series of ultrasound image frames across time. The frame-by-frame classification categorizes each ultrasound image frame into one of multiple categories associated with a first set of clinical characteristics. The time-series vector analysis analyzes the frame-by-frame classification outputs, for example, to determine a classification based on a second set of clinical characteristics. The first set of clinical characteristics and the second set of clinical characteristics can include features representative of different types of diseases or clinical conditions and/or different degrees of severity. The disclosed embodiments may employ a convolutional neural network (CNN) for the frame-by-frame image classification and may employ a machine learning network or model for the time-series vector analysis. The accumulated or integrated classification and analysis results obtained from the frame-by-frame image classification and time-series vector analysis can indicate a particular type of diseases or a level of severity of a particular disease. While the disclosed embodiments are described in the context of lung ultrasound image feature classifications for identifying a lung condition, the disclosed embodiments can be applied to ultrasound images of different organs (e.g., hearts) for identifying different types of diseases.

In one embodiment, a clinical condition detection system includes a communication device in communication with an ultrasound imaging device and configured to receive a sequence of ultrasound image frames representative of a subject body across a time period; and a processor in communication with the communication device and configured to classify the sequence of ultrasound image frames into a first set of clinical characteristics by applying a first predictive network to the sequence of ultrasound image frames to produce a set of classification vectors representing the first set of clinical characteristics; and identify a clinical condition of the subject body by applying a second predictive network to the set of classification vectors.

In some embodiments, the processor is further configured to classify the sequence of ultrasound image frames by applying the first predictive network to each ultrasound image frame of the sequence of ultrasound image frames to generate one classification vector of the set of classification vectors. In some embodiments, the first predictive network is a convolutional neural network, and wherein each classification vector includes a plurality of scores for a corresponding ultrasound image frame with respect to the first set of clinical characteristics. In some embodiments, the processor is further configured to identify the clinical condition by generating, by the second predictive network, a plurality of scores for the set of classification vectors with respect to a second set of clinical characteristics; and selecting a highest score from the plurality of scores. In some embodiments, the first set of clinical characteristics is identical to the second set of clinical characteristics. In some embodiments, the first set of clinical characteristics is associated with different types of clinical features, and wherein the second set of clinical characteristics is associated with different degrees of severity for at least one of the different types of clinical features. In some embodiments, the first set of clinical characteristics is associated with a first categorization of at least one of different types of clinical features or different degrees of severity, and wherein the second set of clinical characteristics is associated with a second categorization of the at least one of the different types of clinical features or the different degrees of severity. In some embodiments, the subject body includes at least a portion of a lung. In some embodiments, the clinical condition includes features associated with at least one of a normal lung, a B-line artifact, consolidation, a bronchogram, or a pleural effusion. In some embodiments, the clinical condition includes features associated with a degree of severity of at least one of a normal lung, a B-line artifact, consolidation, a bronchogram, or a pleural effusion. In some embodiments, at least the first predictive network or the second predictive network is trained by providing a plurality of scan-formatted ultrasound images representative of test subject bodies including the clinical condition captured by different ultrasound imaging devices; converting the plurality of scan-formatted ultrasound images into a plurality of pre-scan-formatted ultrasound images based on at least one of a common dimension or a common format independent of the different ultrasound imaging devices; and assigning a score to each ultrasound image of the plurality of pre-scan-formatted ultrasound images with respect to the clinical condition. In some embodiments, the different ultrasound imaging devices include at least one of a linear ultrasound transducer device, curvilinear ultrasound transducer device, or a phased-array ultrasound transducer device. In some embodiments, the system further comprises a display in communication with the processor and configured to display an indication of the clinical condition.

In one embodiment, a method for clinical condition detection includes receiving, from an ultrasound imaging device, a sequence of ultrasound image frames representative of a subject body across a time period; classifying the sequence of ultrasound image frames into a first set of clinical characteristics by applying a first predictive network to the sequence of ultrasound image frames to produce a set of classification vectors associated with the first set of clinical characteristics; and identifying a clinical condition of the subject body by applying a second predictive network to the set of classification vectors.

In some embodiments, the classifying includes applying the first predictive network to each ultrasound image frame of the sequence of ultrasound image frames to generate one classification vector of the set of classification vectors. In some embodiments, the first predictive network is a convolutional neural network, and wherein each classification vector includes a plurality of scores for a corresponding ultrasound image frame with respect to the first set of clinical characteristics. In some embodiments, the identifying includes generating, by the second predictive network, a plurality of scores for the set of classification vectors with respect to a second set of clinical characteristics; and selecting a highest score from the plurality of scores. In some embodiments, the subject body includes at least a portion of a lung, and wherein the clinical condition includes features associated with at least one of a normal lung, a B-line artifact, consolidation, a bronchogram, or a pleural effusion. In some embodiments, the subject body includes at least a portion of a lung, and wherein the clinical condition includes features associated with a degree of severity of at least one of a normal lung, a B-line artifact, consolidation, a bronchogram, or a pleural effusion. In some embodiments, the method further comprises displaying, by a display, an indication of the clinical condition.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
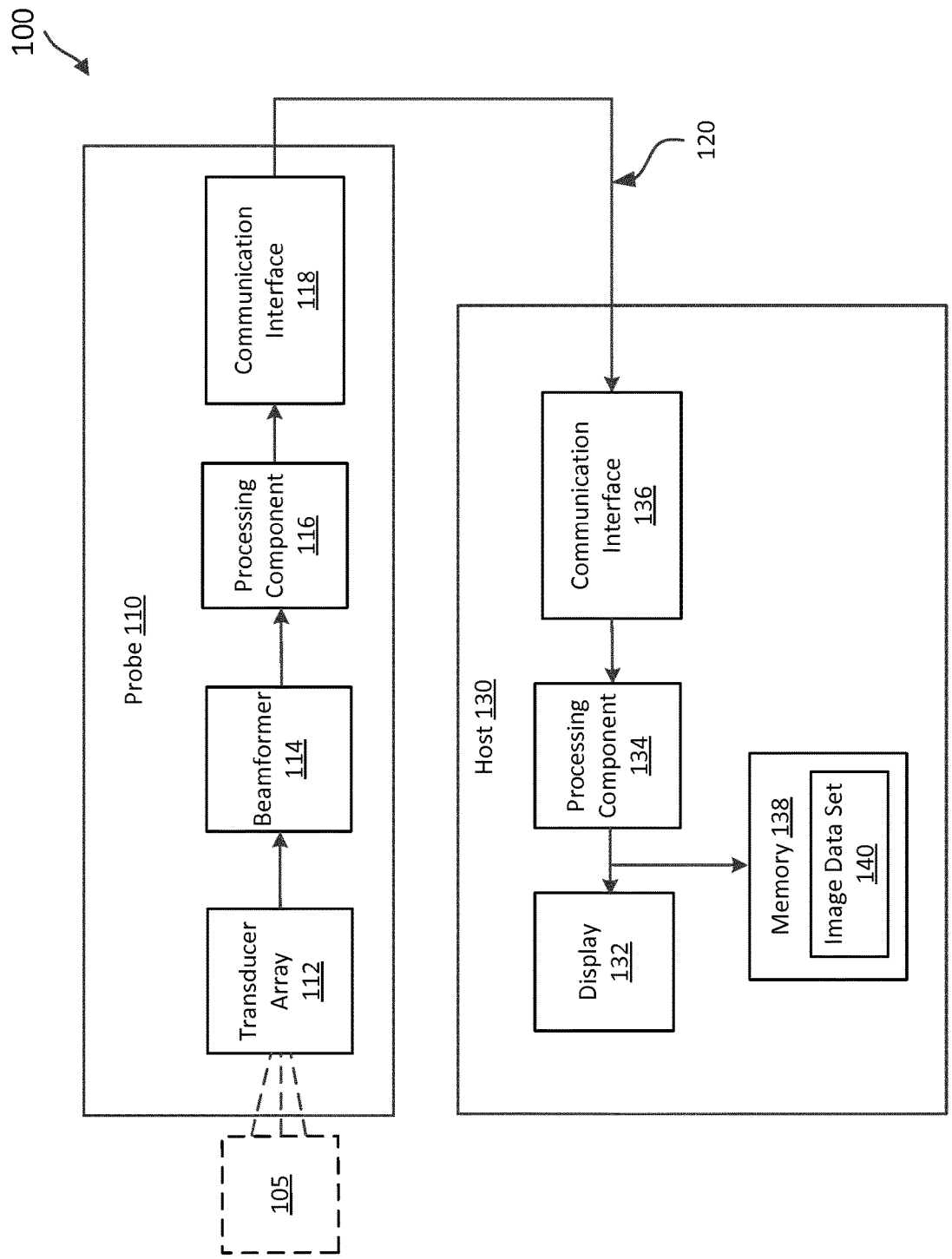
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer 112, a beamformer 114, a processing component 116, and a communication interface 118. The host 130 includes a display 132, a processing component 134, and a communication interface 136.

The transducer 112 emits ultrasound signals towards an anatomical object 105 and receives echo signals reflected from the object 105 back to the transducer 112. The ultrasound transducer 112 can include any suitable number of acoustic elements, including one or more acoustic elements and/or plurality of acoustic elements. In some instances, the transducer 112 includes a single acoustic element. In some instances, the transducer 112 may include an array of acoustic elements with any number of acoustic elements in any suitable configuration. For example, the transducer 112 can include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer 112 can be configured to obtain one-dimensional, two-dimensional, and/or three-dimensional images of patient anatomy. In some embodiments, the ultrasound imaging element 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer array 112 in combination with the beamformer 114 may be referred to as an ultrasound imaging component. In some embodiments, the object 105 may include at least a portion of a patient's lung for a lung ultrasound examination. In other embodiments, the object 105 may include any anatomy (e.g., blood vessel, heart, kidney, and/or liver) of a patient that is suitable ultrasound imaging examination.

The processing component 116 is coupled to the beamformer 114. The processing component 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 116 is configured to process the beamformed image signals. For example, the processing component 116 may perform filtering and/or quadrature demodulation to condition the image signals.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processing component 134 is coupled to the communication interface 136. The processing component 134 may be implemented as a combination of software components and hardware components. The processing component 134 may include a central processing unit (CPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 can perform real-time processing on the image data to provide a streaming video of ultrasound images of the object 105.

In some embodiments, the processing component 134 may perform scan format conversion on the image data. For example, the processing component 134 may interpolate the image data to displayed data. The image data can be in various formats depending on the types of transducers (e.g., the transducer array 112) or probes used for capturing the image signals. Some examples of probe types may include linear, curvilinear, and phased-array. A linear probe may include an array of transducers arranged in a linear array configuration. A curvilinear probe may include an array of transducers arranged in a curvilinear or convex configuration. A phased-array probe may include an array of transducers that can produce steerable and focused beams (e.g., based on delay and phase controls). When the probe 110 is a linear probe (e.g., the transducer array 112 arranged in a linear configuration), the image data may be in Cartesian coordinates. When the probe 110 is a curvilinear probe (e.g., the transducer array 112 arranged in a curvilinear configuration) or phased-array probe (e.g., the transducer array 112 with delays and phase controls), the image data may be in polar coordinates. The processing component 134 can perform coordinate transformation on the image data to produce scan-formatted image frames for display, as described in greater detail herein.

In some embodiments, the processing component 134 can perform image analysis on the image data or image frames for clinical assessments. For example, the processing component 134 can apply deep-learning-based techniques to perform clinical assessments based on the image data or image frames, as described in greater detail herein.

The display 132 is coupled to the processing component 134. The display 132 may be a monitor or any suitable display. The display 132 is configured to display ultrasound images, image videos, and/or diagnostic results processed by the processing component 134.

The system 100 can be configured for use in various stages of ultrasound imaging feature detections for clinical assessments. In an embodiment, the system 100 may be used for collecting ultrasound images to form training data set. For example, the host 130 may include a memory 138, which may be any suitable storage device, such as a cache memory (e.g., a cache memory of the processing component 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store an image data set 140 including the scan-formatted image frames for deep learning-based training.

In some embodiments, the system 100 may be used for training deep learning networks for clinical feature detections and assessments. The training data set 140 may be converted into a certain format, for example, a pre-scan format, suitable for training. The pre-scan formatted data set can be used to train a deep learning network to classify features in ultrasound images or video captured by the probe 110 with respect to certain clinical features and/or conditions.

In some embodiments, the system 100 may be used in a clinical setting for live ultrasound examinations, where the trained deep learning networks may be applied to determine a clinical condition. Mechanisms for automatically and systematically detecting clinical features and/or conditions from ultrasound images based on learning-based techniques are described in greater detail herein.

Figure 2:
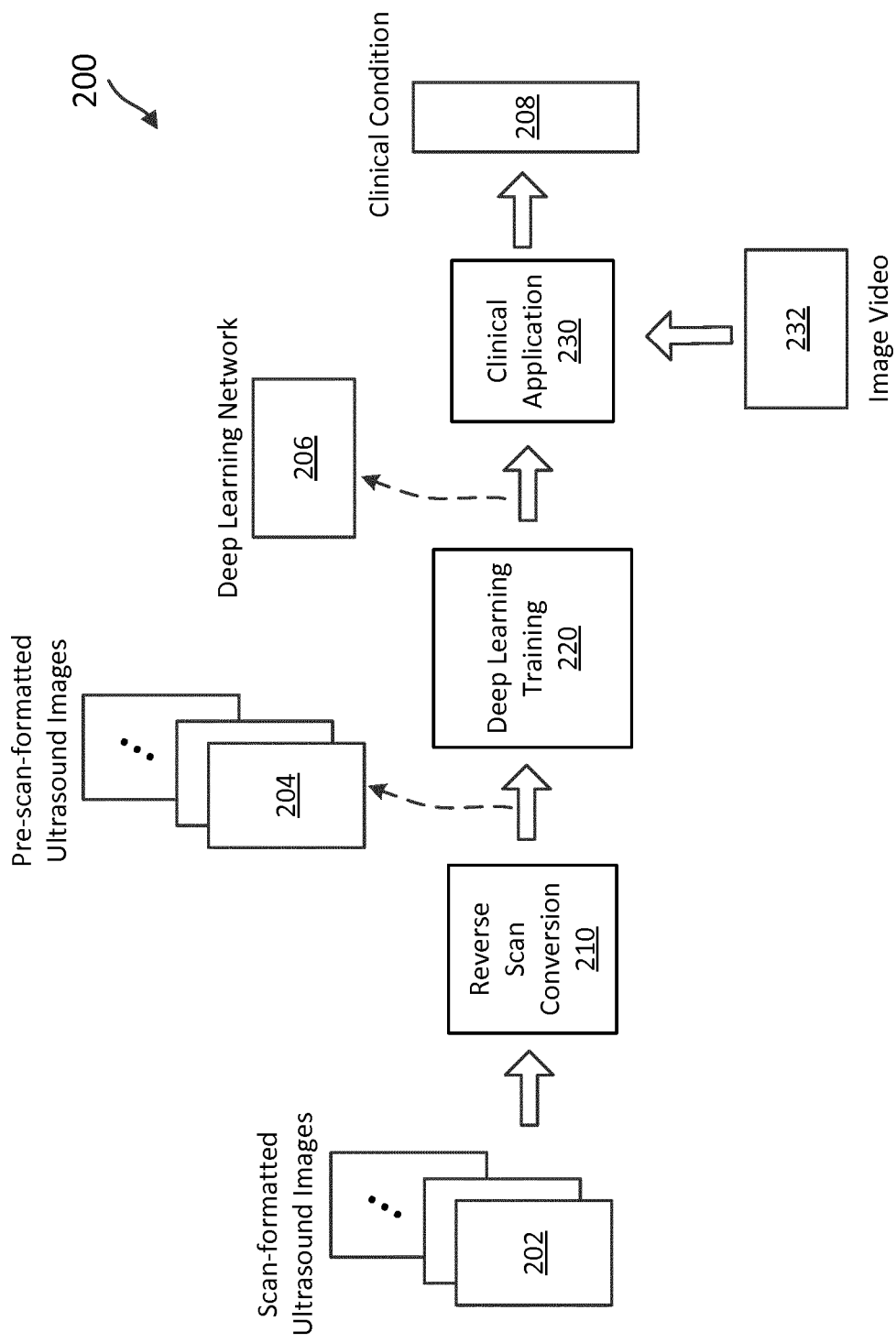
FIG. 2 is a schematic diagram illustrating an ultrasound image feature detection scheme, according to aspects of the present disclosure.

FIG. 2 is a schematic diagram illustrating an ultrasound image feature detection scheme 200, according to aspects of the present disclosure. The scheme 200 can be employed by the system 100 for various stages of ultrasound image feature detection. The scheme 200 employs deep learning-based techniques to extract clinical features from ultrasound images and/or videos and to classify the clinical features for clinical assessments. The scheme 200 includes a reverse scan conversion stage 210, a deep learning training stage 220, and a clinical application stage 230. The reverse scan conversion stage 210 formats ultrasound images acquired using different ultrasound probes (e.g., linear probes, curvilinear probes, and phased-array probes) into a common image format and/or dimensions suitable for training deep learning networks. The deep learning network stage 220 trains deep learning networks to classify ultrasound images into clinical feature categories suitable for clinical assessments, for example, using training data output by the reverse scan conversion stage 210. The clinical application stage 230 applies the trained deep learning networks to a live or real-time ultrasound imaging video captured from a patient to identify a clinical condition of the patient. The scheme 200 will be described below with reference to FIGS. 3A, 3B, 3C, 4A, 4B, 4C, 4D, 4E, 5, and 6.

At the reverse scan conversion stage 210, scan-formatted ultrasound images 202 are converted into pre-scan-formatted ultrasound images 204. The scan-formatted ultrasound images 202 may correspond to the scan-formatted images generated by the processing component 134 and stored as a training data set 140 in the memory 138. As described above, ultrasound images may be captured by various types of transducer probes (e.g., the probe 110), such as linear probes, curvilinear probes, and phased-array probes. Due to probe geometry and imaging format differences, ultrasound images can have different sizes and/or image shapes. The difference sizes and/or image shapes may not carry useful or meaningful clinical information. On the contrary, the image format differences or variations can impact or bias the training of deep learning networks for clinical feature classifications.

The reverse scan conversion re-formats the scan-formatted images 202 obtained from various types of probes into ultrasound images of the same format or same dimensions regardless of the transducer types and/or imaging configuration such as imaging depth and/or field-of-view angle. The reverse scan conversion can include image portions or regions that are significant for clinical classifications and exclude image portions or regions that can impact the training. For example, in lung ultrasound, a certain lung condition is determined based the presence or absence of certain clinical features, such as B-line artifacts, consolidation, pleural effusion, and/or bronchogram, in an ultrasound image, and not based on the length and/or area of the geometry of the image.

Figure 3A:
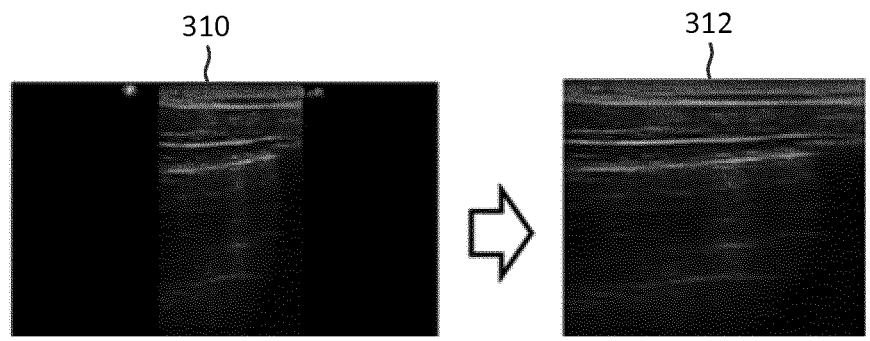
FIG. 3A are ultrasound images of a patient's lung before and after a reverse scan conversion, according to aspects of the present disclosure.

FIG. 3A are ultrasound images and of a patient's lung before and after a reverse scan conversion, according to aspects of the present disclosure. The ultrasound image 310 is captured by a linear probe and scan-formatted as described above. As shown, the ultrasound image 310 shows an image of the lung in a rectangular shape since a linear probe emits parallel ultrasound beams. The ultrasound image 312 corresponds to the ultrasound image 310 after a reverse scan conversion. For example, the ultrasound image 310 may correspond to a scan-formatted image 202 and the ultrasound image 312 may correspond to a pre-scan-formatted image 204.

Figure 3B:
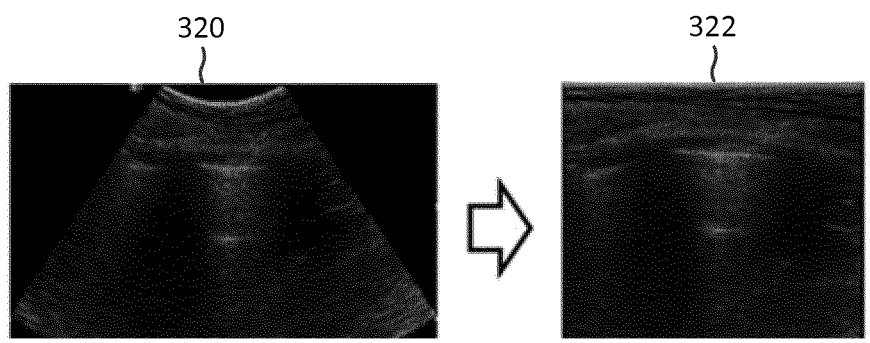
FIG. 3B are ultrasound images of a patient's lung before and after a reverse scan conversion, according to aspects of the present disclosure.

FIG. 3B are ultrasound images of a patient's lung before and after a reverse scan conversion, according to aspects of the present disclosure. The ultrasound image 320 is captured by a curvilinear probe and scan-formatted as described above. As shown, the ultrasound image 320 shows an image of the lung in a sector shape or a pie shape since a curvilinear probe emits ultrasound beams at different angles or directions that diverge. The ultrasound image 322 corresponds to the ultrasound image 320 after a reverse scan conversion. For example, the ultrasound image 320 may correspond to a scan-formatted image 202 and the ultrasound image 322 may correspond to a pre-scan-formatted image 204.

Figure 3C:
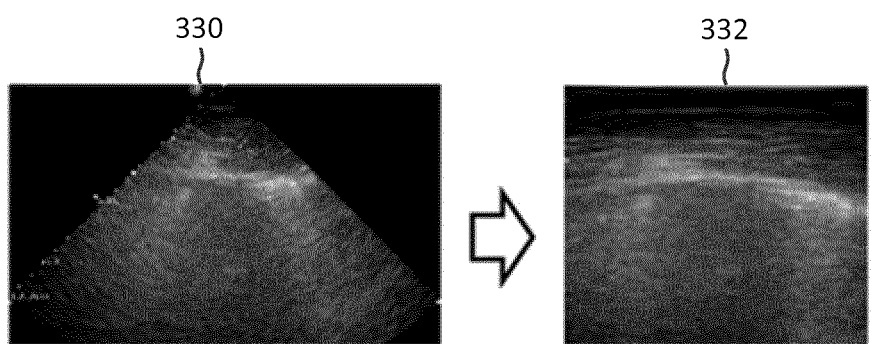
FIG. 3C are ultrasound images of a patient's lung before and after a reverse scan conversion, according to aspects of the present disclosure.

FIG. 3C are ultrasound images of a patient's lung before and after a reverse scan conversion, according to aspects of the present disclosure. The ultrasound image 330 is captured by a phased-array probe and scan-formatted as described above. As shown, the ultrasound image 330 shows an image of the lung in a sector shape or a pie shape since a phased-array probe applies electronic steering to focus ultrasound beams at various angles or directions. The ultrasound image 332 corresponds to the ultrasound image 330 after a reverse scan conversion. For example, the ultrasound image 330 may correspond to a scan-formatted image 202 and the ultrasound image 332 may correspond to a pre-scan-formatted image 204.

As can be seen from FIGS. 3A-3C, the ultrasound images 312, 322, and 332 exclude the probe-specific image features (e.g., the pie shape or sector shape) from the images 310, 320, and 330, respectively. In other words, the reverse scan conversion converts a scan-formatted image back to the pre-scan format. In addition, the reverse scan conversion removes the dark portions or regions of the images 310, 320, and 330 that do not include portions of the lung.

While the scheme 200 is illustrated with the reverse scan conversion stage 210, in some embodiments, the reverse scan conversion stage 210 can be optional. For example, the host 130 can store the processed image data before the scan format conversion in the memory 138 instead of or in addition to the scan-formatted image frames. In other words, the host 130 can store pre-scan-formatted ultrasound images 204 in the memory 138. Thus, the pre-scan formatted ultrasound images 204 are available for use by the scheme 200 without the need for the reverse scan conversion stage 210.

At the deep learning training stage 220, the pre-scan-formatted ultrasound images 204 can be used to train a deep learning network 206. For example, the pre-scan-formatted ultrasound images 204 may be lung images including various visible structures and/or artifacts that indicate certain lung conditions. The deep learning network 206 can be trained to recognize certain imaging features or artifacts useful for determining a particular clinical condition or disease. For example, the deep learning network 206 can be trained to classify the pre-scan-formatted ultrasound images 204 into multiple categories of clinical significances. FIGS. 4A-4E illustrate various clinical features that are useful for lung ultrasound examination or assessments.

Figure 4A:
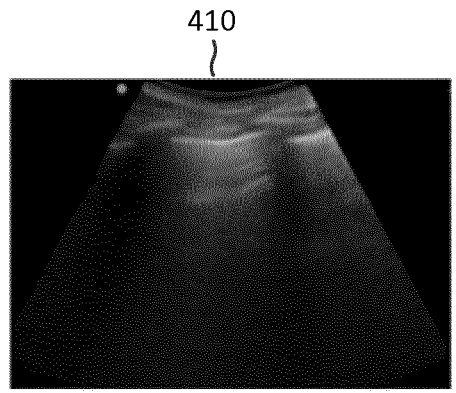
FIG. 4A is an ultrasound image illustrating a normal lung condition, according to aspects of the present disclosure.
Figure 4B:
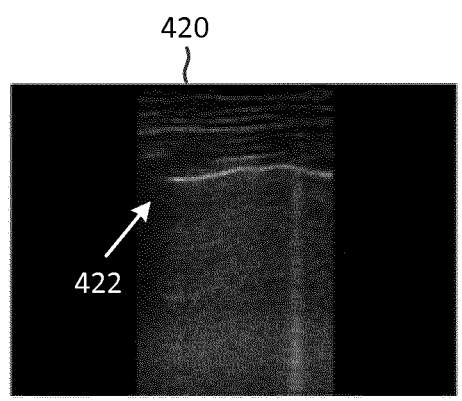
FIG. 4B is an ultrasound image frame illustrating B-line artifacts, according to aspects of the present disclosure.

FIG. 4A is an ultrasound image 410 illustrating a normal lung condition, according to aspects of the present disclosure. FIG. 4B is an ultrasound image 420 illustrating B-line artifacts, according to aspects of the present disclosure. The ultrasound image 420 includes multiple white lines 422 that are about horizontal, which are referred to as B-line artifacts, in the lung that are absence under the normal condition shown in the ultrasound image 410. The B-line artifacts may represent a sign of increased density due to the loss of aeration in the lung periphery.

Figure 4C:
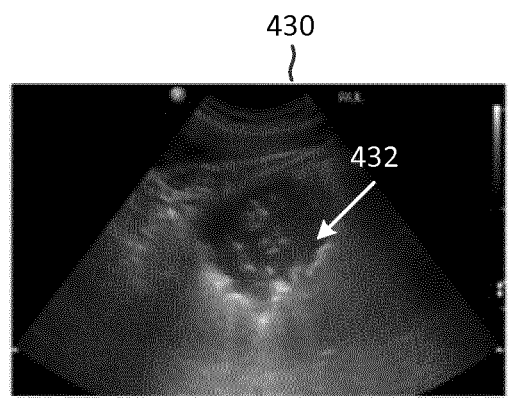
FIG. 4C is an ultrasound image frame illustrating a consolidation, according to aspects of the present disclosure.

FIG. 4C is an ultrasound image 430 illustrating a consolidation, according to aspects of the present disclosure. The ultrasound image 430 includes a wedge-shaped region 432 that appears solid and uniformly hypoechoic in the lung that is absence under the normal condition shown in the ultrasound image 410. The hypoechoic wedge-shaped region 432 may be indicative of a lung consolidation condition.

Figure 4D:
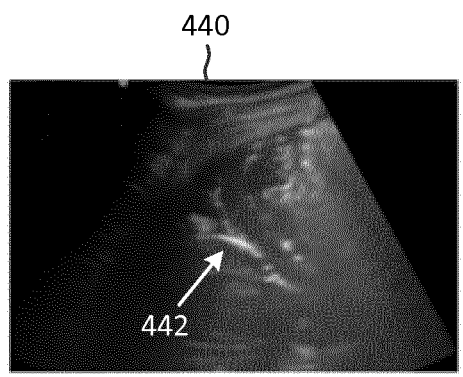
FIG. 4D is an ultrasound image frame illustrating an air bronchogram, according to aspects of the present disclosure.

FIG. 4D is an ultrasound image 440 illustrating an air bronchogram, according to aspects of the present disclosure. The ultrasound image 440 includes a bright tubular structure 442 in the lung that is absence under the normal condition shown in the ultrasound image 410. The tubular structure 442 may be indicative of a lung bronchogram condition.

Figure 4E:
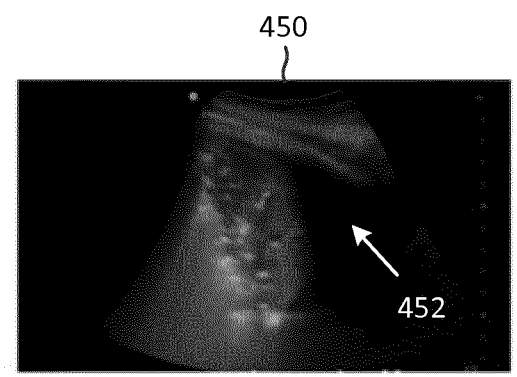
FIG. 4E illustrates an ultrasound image frame illustrating a pleural effusion, according to aspects of the present disclosure.

FIG. 4E illustrates an ultrasound image 450 illustrating a pleural effusion, according to aspects of the present disclosure. The ultrasound image 450 includes an anechoic area 452 in the lung that is absence under the normal condition shown in the ultrasound image 410. The anechoic area 452 may be indicative of a lung pleural effusion condition.

The deep learning network 206 can include multiple stages or layers of deep learning or multiple deep learning sub-networks. The different layers or different sub-networks may perform feature analysis and/or classifications in different domains (e.g., including a spatial domain and a time domain) as described in greater detail herein. Deep learning may include various learning-based techniques, such as machine learning and convolutional neural networks (CNNs), that use non-linear processing and feature extraction and/or transformation for classifications or pattern analysis. For example, the deep learning network 206 can be trained to classify lung ultrasound images into multiple categories to facilitate identification of lung conditions. The categories may be similar to the features and/or conditions (e.g., normal, B-line artifacts, consolidation, bronchogram and/or pleural effusion) described above with respect to FIGS. 4A-4E. As an example, the deep learning network 206 may include a CNN (e.g., the CNN 510 in FIG. 5 and the CNN 612 in FIG. 6) that performs frame-by-frame analysis and a machine learning component (e.g., the machine learning component 614 in FIG. 6) that performs temporal analysis on the frame-by-frame analysis output.

Figure 5:
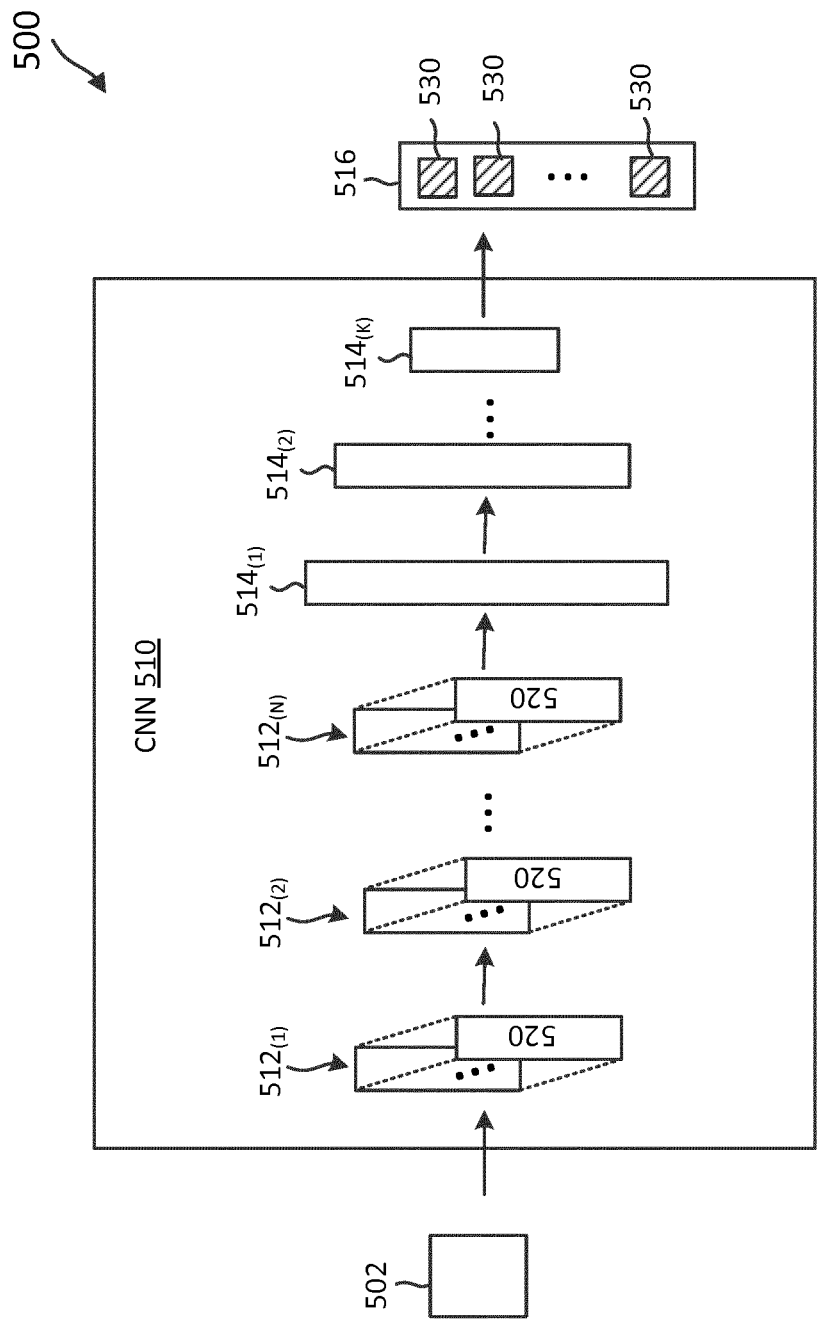
FIG. 5 is a schematic diagram illustrating a configuration of a convolutional neural network (CNN), according to aspects of the present disclosure.

FIG. 5 is a schematic diagram illustrating a configuration 500 of a CNN 510, according to aspects of the present disclosure. The CNN 510 can be employed by the scheme 200 for frame-by-frame classification. The CNN 510 may include a set of N convolutional layers 512 followed by a set of K fully connected layers 514, where N and K may be any positive integers. The values N and K may vary depending on the embodiments. In some embodiments, both N and K may be at least 3. Each convolutional layer 512 may include a set of filters 520 configured to extract imaging features (e.g., one-dimensional (1D) feature maps) from an input image. The fully connected layers 514 may be non-linear and may gradually shrink the high-dimensional output of the last convolutional layer $512_{(N)}$ to a length corresponding to the number of classifications 530 at the output 516. For example, the classifications 530 may include a normal lung condition, B-line artifacts, a consolidation, a bronchogram, and a pleural effusion.

While not shown in FIG. 5, in some embodiments, the convolutional layers 512 may be interleaved with pooling layers, each including a set of downsampling operations that may reduce the dimensionality of the extracted imaging features. In addition, the convolutional layers 512 may include non-linearity functions (e.g., including rectified non-linear (ReLU) operations) configured to extract rectified feature maps.

An input image 502 (e.g., the pre-scan-formatted ultrasound image 204) may be passed through each layer 512 and 514 in succession for feature extraction, analysis, and/or classification. Each layer 512 or 514 may include weightings (e.g., filter coefficients for the filters 520 in the convolutional layers 512 and non-linear weightings for the fully-connected layers 514) that are applied to the input image 502 or an output of a previous layer 512 or 514.

During training, the CNN 510 can be applied to each pre-scan-formatted image 204, for example, using forward propagation, to obtain an output or a score for the pre-scan-formatted image 204 for each category or classification 530. The coefficients of the filters 520 in the convolutional layers 512 and weightings in the fully connected layers 514 can be adjusted, for example, by using backward propagation to minimize the output error. For example, an input image 502 including B-line artifacts can be used to train the CNN 510 such that the CNN 510 may output a high probability (e.g., greater that 90%) for the B-line category.

The machine learning component can include the same architecture or a different architecture as the CNN 510. The machine learning component can be trained using substantially similar mechanisms, where the training is to ensure that the machine learning component can produce an output with a high classification accuracy. Mechanisms for the frame-by-frame analysis and the temporal analysis are described in greater detail herein.

After the deep learning network 206 is trained, the deep learning network 206 can be used in the clinical application stage 230. For example, a clinician or a user may use the system 100 to capture an image video 232 of a patient's lung. The host 130 can receive the image video 232 in real-time. The processing component 134 on the host 130 can apply the trained deep learning network 206 to the image video 232 to determine a clinical condition 208 of the patient.

Figure 6:
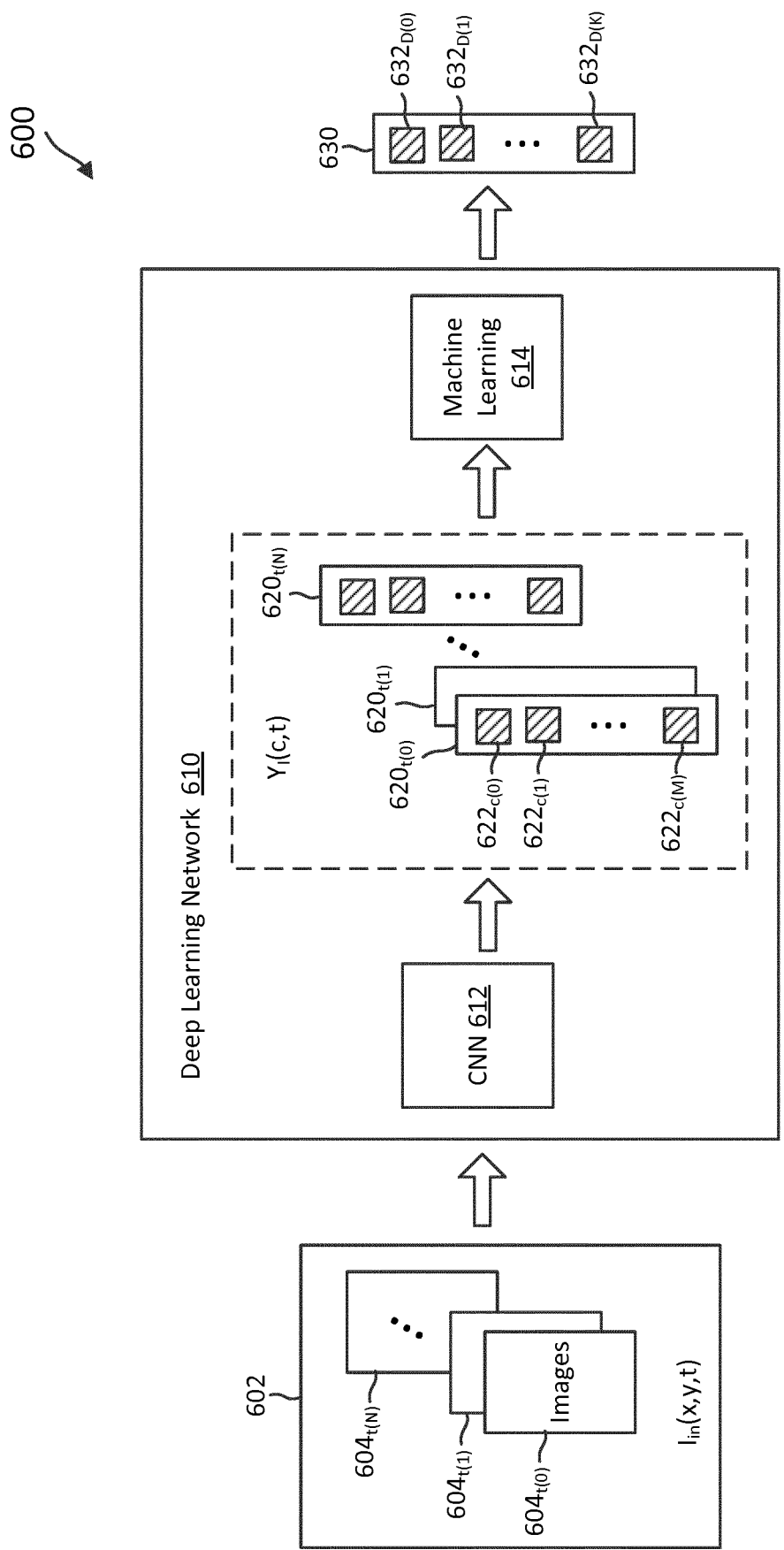
FIG. 6 is a schematic diagram illustrating a configuration of a deep learning network for ultrasound image feature detection, according to aspects of the present disclosure.

FIG. 6 is a schematic diagram illustrating a configuration 600 of a deep learning network 610 for ultrasound image feature detection, according to aspects of the present disclosure. The deep learning network 610 may correspond to the deep learning network 206. The deep learning network 610 can predict a clinical condition given an input image video 602. The deep learning network 610 includes a CNN 612 (e.g., the CNN 510) and a machine learning component 614. The deep learning network 610 can be implemented using a combination of hardware components and software components. For example, the deep learning network 610 can be implemented by the processing component 134 to perform real-time classifications of clinical features and/or conditions. The CNN 612 can be trained to perform frame-by-frame analysis or classifications in a spatial domain. The machine learning component 614 can be trained to perform time-series vector classifications.

The deep learning network 610 is configured to receive an ultrasound image video 602, for example, captured using the system 100. The video 602 may correspond to the video 232. The video 602 may include a sequence of ultrasound image frames 604 representative of a patient (e.g., at least a portion of a lung) across a time period, for example, at time instants t(0), t(1), t(N), where N is a positive integer. The ultrasound image frames 604 are shown as $604_{t(0)}$, $604_{t(1)}$, ... $604_{t(N)}$. For example, the sequence of ultrasound image frames 604 can be represented by $I_{in}(x,y,t)$, where x and y may represent a spatial domain and t can represent time varying from 1 to N. The ultrasound image frames 604 may be similar to the ultrasound images 310, 320, 330, 410, 420, 430, 440, 450, and 502.

To perform frame-by-frame analysis, the CNN 612 is applied to each ultrasound image frame 604. The CNN 612 produces an output vector 620 for each ultrasound image frame 604. The output vectors 620 are shown as $620_{t(0)}$, $620_{t(1)}$, ... $620_{t(N)}$ corresponding to outputs for the ultrasound image frames $604_{t(0)}$, $604_{t(1)}$, ... $604_{t(N)}$, respectively. The output vectors 620 may be similar to the output 516. Each output vector 620 may include (M+1) scores or values 622, where M is a positive integer. Each value 622 represents the likelihood or the probability of an input ultrasound image frame 604 being classified into a particular category (e.g., including a certain clinical feature or a clinical condition). The categories may be represented by C(0) to C(M). The output values 622 or probabilities for the (M+1) categories are shown as $622_{C(0)}$, $622_{C(1)}$, ... $622_{C(M)}$. For example, the set of output vectors 620 can be represented by $Y_f(c,t)$, where c may represent category indices varying from 1 to M and t can represent time varying from 1 to N.

When applying the CNN 612 in the lung condition assessment example described above, M can be about 4. For example, the category C(0) can represent a normal lung condition, the category C(1) can represent a B-line artifact condition, the category C(2) can represent a lung consolidation condition, the category C(3) can represent a bronchogram condition, and the category C(4) can represent a pleural effusion lung condition. In other words, the CNN 612 can be applied to an input image frame 604 to determine whether the input image frame 604 includes an image with a normal condition, a B-line artifact condition, a lung consolidation condition, a bronchogram condition, or a pleural effusion condition. The CNN 612 can produce an output vector 620 indicating a probability for each lung condition.

To perform time-domain analysis, the machine learning component 614 is applied to the set of output vectors 620 (e.g., a (M+1) by (N+1) matrix). The machine learning component 614 produces an output vector 630 including include (K+1) scores or values 632, where K is a positive integer. Each value 632 represents the likelihood or the probability of the video 602 being classified into a particular category (e.g., including a certain clinical feature or a clinical condition). The categories may be represented by D(0) to D(K). The output values 632 or probabilities for the (K+1) categories are shown as $632_{D(0)}$, $632_{D(1)}$, ... $632_{D(K)}$. The machine learning component 614 can employ any suitable learning-based techniques for the classification. In some embodiments, the machine learning component 614 can include a deep learning network, a neural network, or a CNN. The category with the greatest probability (e.g., the greatest value 632 in the output vector 630) may be indicative of a classification (e.g., a clinical condition) for the video 602. In some embodiments, the categories C(0) to C(M) output by the CNN 612 may be identical to the categories D(0) to D(K) output by the machine learning component 614. In other words K is equal to M. For example, the categories C(0) to C(M) may correspond to different types of clinical features, such as a normal lung condition, B-line artifacts, consolidation, bronchogram, and pleural effusion. The categories D(0) to D(K) may correspond to the same set of lung features as the categories C(0) to C(M).

In some embodiments, the categories C(0) to C(M) may correspond to different types of clinical features and the categories D(0) to D(M) may correspond to different degrees of severity. For example, the categories C(0) to C(M) may correspond to the different types of lung conditions and the categories D(0) to D(K) may include a normal lung condition, a mild B-line condition, a severe B-line condition, a mild consolidation, and a severe consolidation.

In some embodiments, the categories C(0) to C(M) may correspond to a first categorization of at least one of different types of clinical features or different degrees of severity and the categories D(0) to D(M) may correspond to a second categorization of at least one of different types of clinical features or different degrees of severity.

While the deep learning network 610 is shown to include a CNN 612 and a machine learning component 614, in some embodiments, the deep learning network 610 can include a machine learning component in place of the CNN 612 and/or a CNN in place of the machine learning component 614 to achieve similar functionalities.

Figure 7:
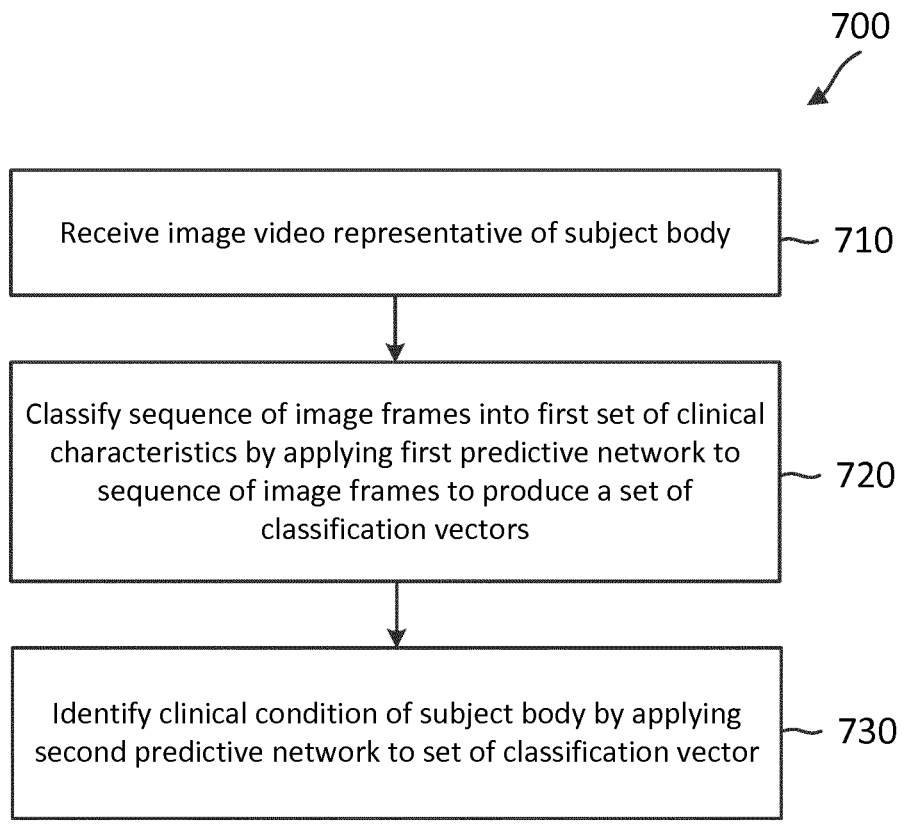
FIG. 7 is a flow diagram of an automated ultrasound image feature detection method, according to aspects of the present disclosure.

FIG. 7 is a flow diagram of an automated ultrasound image feature detection method 700, according to aspects of the present disclosure. Steps of the method 700 can be executed by a computing device (e.g., a processor, processing circuit, and/or other suitable component) of an ultrasound imaging probe, such as the probe 110, or a host such as the host 130. The method 700 may employ similar mechanisms as in the scheme 200 described with respect to FIG. 2 and may employ deep learning-based classification mechanisms as in the configurations 500 and 600 described with respect to FIGS. 5 and 6, respectively. As illustrated, the method 700 includes a number of enumerated steps, but embodiments of the method 700 may include additional steps before, after, and in between the enumerated steps. In some embodiments, one or more of the enumerated steps may be omitted or performed in a different order.

At step 710, the method 700 includes receiving, from an ultrasound imaging device (e.g., the probe 110 or the transducer array 112), a sequence of ultrasound image frames (e.g., the ultrasound image frames 604) representative of a subject body (e.g., the object 105 or a patient's lung, heart, kidney, or liver) across a time period (e.g., from time instants t(0) to t(N)). The sequence of ultrasound image frames may correspond to an image video (e.g., the videos 232 or 602).

At step 720, the method 700 includes classifying the sequence of ultrasound image frames into a first set of clinical characteristics (e.g., the categories C(0) to C(M)) by applying a first predictive network (e.g., the CNNs 510 and 612) to the sequence of ultrasound image frames. The first set of clinical characteristics may be represented by a set of classification vectors (e.g., the output vectors 620).

At step 730, the method 700 includes identifying a clinical condition (e.g., a lung condition) of the subject body by applying a second predictive network (e.g., the machine learning component 614) to the set of classification vectors.

In some embodiments, the method 700 can classify the sequence of ultrasound image frames by applying the first predictive network to each ultrasound image frame of the sequence of ultrasound image frames to generate one classification vector of the set of classification vectors. The first predictive network can be a CNN (e.g., the CNNs 510 and 612), where each classification vector includes a plurality of scores (e.g., the probability values 622) for a corresponding ultrasound image frame with respect to the first set of clinical characteristics.

In some embodiments, the method 700 can identify the clinical condition by generating, by the second predictive network, a plurality of scores (e.g., the probability values 632) for the set of classification vectors with respect to a second set of clinical characteristics (e.g., the categories D(0) to D(K)), and selecting a highest score from the plurality of scores. The category with the highest score may represent the integrated classification result (e.g., the clinical condition).

In some embodiments, the subject body may include at least a portion of a lung, and wherein the clinical condition includes features associated with at least one of a normal lung (e.g., the ultrasound image 410), a B-line artifact (e.g., the ultrasound image 420), consolidation (e.g., the ultrasound image 430), a bronchogram(e.g., the ultrasound image 440), or a pleural effusion (e.g., the ultrasound image 450).

In some embodiments, the subject body includes at least a portion of a lung, and wherein the clinical condition includes features associated with a degree of severity of at least one of a normal lung, a B-line artifact, consolidation, a pleural effusion, or a bronchogram.

In some embodiments, the method 700 includes displaying, by a display (e.g., the display 132), an indication of the clinical condition.

In some embodiments, at least the first predictive network or the second predictive network is trained by providing a plurality of scan-formatted ultrasound images (e.g., the scan-formatted ultrasound images 202) representative of test subject bodies including the clinical condition captured by different ultrasound imaging devices. The different ultrasound imaging devices can include at least one of a linear ultrasound transducer device, curvilinear ultrasound transducer device, or a phased-array ultrasound transducer device. The training further include converting the plurality of scan-formatted ultrasound images into a plurality of pre-scan-formatted ultrasound images (e.g., the pre-scan-formatted ultrasound images 204 and 502) based on at least one of a common dimension or a common format independent of the different ultrasound imaging devices. The training can further include assigning a score to each ultrasound image of the plurality of pre-scan-formatted ultrasound images with respect to the clinical condition.

Aspects of the present disclosure can provide several benefits. For example, the classification of a video by dividing the classification into a spatial domain frame-by-frame classification and a temporal domain analysis can reduce the classification complexity compared to traditional machine learning-based video classification framework. The dividing of the classification problem into multiple stages can allow training to be performed using a smaller training dataset than traditional video classification machine learning-based networks. The use of deep learning networks can automate clinical condition assessments, providing assistances to guide clinicians in determining clinical conditions. In addition, the automating can provide more consistent assessment results, eliminating variations that can arise from different interpretations across different clinicians. Further, the automating can allow for monitoring of a patient for a particular clinical condition over time, for example, to evaluate the progress of a certain disease or the benefits of a certain treatment.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A clinical condition detection system, comprising:
   a communication device in communication with an ultrasound imaging device and configured to receive a sequence of ultrasound image frames representative of a subject body across a time period; and
   a processor in communication with the communication device and configured to:
      classify spatial domain information in the sequence of ultrasound image frames by applying a first deep learning network to each ultrasound image frame of the sequence of ultrasound image frames to generate, for each of the image frames, a classification vector including a probability for each clinical characteristic of a first set of clinical characteristics, wherein the first set of clinical characteristics is associated with different types of clinical features, wherein the first deep learning network is a convolutional neural network;
      classify time domain information in the classification vectors corresponding to the sequence of ultrasound image frames across the time period by applying a second deep learning network to generate a probability for each clinical characteristic of a second set of clinical characteristics, wherein the second set of clinical characteristics is associated with different degrees of severity for at least one of the different types of clinical features, wherein the second deep learning network is a machine learning network, and wherein each probability for each clinical characteristic of a second set of clinical characteristics comprises a probability of the entire sequence of ultrasound image frames video being classified into a particular clinical condition; and identify a clinical condition of the subject body based on the probabilities for the second set of clinical characteristics, wherein the processor is configured to identify the clinical condition by selecting a highest probability from the generated probabilities for the second set of clinical characteristics.

2. The system of claim 1, wherein the first set of clinical characteristics is associated with a first categorization of at least one of different types of clinical features or different degrees of severity, and wherein the second set of clinical characteristics is associated with a second categorization of the at least one of the different types of clinical features or the different degrees of severity.

3. The system of claim 1, wherein the subject body includes at least a portion of a lung.

4. The system of claim 3, wherein the clinical condition includes features associated with at least one of a normal lung, a B-line artifact, consolidation, a bronchogram, or a pleural effusion.

5. The system of claim 3, wherein the clinical condition includes features associated with a degree of severity of at least one of a normal lung, a B-line artifact, consolidation, a bronchogram, or a pleural effusion.

6. The system of claim 1, wherein at least the first deep learning network or the second deep learning network is trained by:
providing a plurality of scan-formatted ultrasound images representative of test subject bodies including the clinical condition captured by different ultrasound imaging devices;
converting the plurality of scan-formatted ultrasound images into a plurality of pre-scan-formatted ultrasound images based on at least one of a common dimension or a common format independent of the different ultrasound imaging devices; and
assigning a score to each ultrasound image of the plurality of pre-scan-formatted ultrasound images with respect to the clinical condition.

7. The system of claim 6, wherein the different ultrasound imaging devices include at least one of a linear ultrasound transducer device, curvilinear ultrasound transducer device, or a phased-array ultrasound transducer device.

8. The system of claim 1, further comprising:
a display in communication with the processor and configured to display an indication of the clinical condition.

9. A method for clinical condition detection, comprising:
receiving, from an ultrasound imaging device, a sequence of ultrasound image frames representative of a subject body across a time period;
classifying spatial domain information in the sequence of ultrasound image frames by applying a first deep learning network to each ultrasound image frame of the sequence of ultrasound image frames to generate, for each of the image frames, a classification vector including a probability for each clinical characteristic of a first set of clinical characteristics, wherein the first set of clinical characteristics is associated with different types of clinical features, wherein the first deep learning network is a convolutional neural network;
classifying time domain information in the classification vectors corresponding to the sequence of ultrasound image frames across the time period by applying a second deep learning network to generate a probability for each clinical characteristic of a second set of clinical characteristics, wherein the second set of clinical characteristics is associated with different degrees of severity for at least one of the different types of clinical features, wherein the second deep learning network is a machine learning network, and wherein each probability for each clinical characteristic of a second set of clinical characteristics comprises a probability of the entire sequence of ultrasound image frames video being classified into a particular clinical condition; and
identifying a clinical condition of the subject body based on the probabilities for the second set of clinical characteristics, comprising selecting a highest probability from the generated probabilities for the second set of clinical characteristics.

10. The method of claim 9, wherein the subject body includes at least a portion of a lung, and wherein the clinical condition includes features associated with at least one of a normal lung, a B-line artifact, consolidation, a bronchogram, or a pleural effusion.

11. The method of claim 9, wherein the subject body includes at least a portion of a lung, and wherein the clinical condition includes features associated with a degree of severity of at least one of a normal lung, a B-line artifact, consolidation, a bronchogram, or a pleural effusion.

12. The method of claim 9, further comprising:
displaying, by a display, an indication of the clinical condition.

* * * * *